US008623646B2

(12) United States Patent  (10) Patent No.: US 8,623,646 B2
Birk et al.  (45) Date of Patent: Jan. 7, 2014

(54) VOLUME EXCLUSION AGENT TO ENHANCE FORMATION OF EXTRACELLULAR MATRIX

(75) Inventors: David E. Birk, Tampa, FL (US); John Hassell, Tampa, FL (US); Bradley Kane, Lakeland, FL (US); La Tia Etheredge, Tampa, FL (US)

(73) Assignees: University of South Florida, Tampa, FL (US); Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 13/035,504

(22) Filed: Feb. 25, 2011

(65) Prior Publication Data

US 2011/0244570 A1  Oct. 6, 2011

Related U.S. Application Data

(63) Continuation of application No. PCT/US2009/054899, filed on Aug. 25, 2009.

(60) Provisional application No. 61/091,584, filed on Aug. 25, 2008.

(51) Int. Cl.
C12N 5/071 (2010.01)
C12N 5/0775 (2010.01)
C12N 5/077 (2010.01)

(52) U.S. Cl.
USPC ............ 435/375; 435/325; 435/405; 435/1.1; 435/41; 435/70.1; 435/70.3

(58) Field of Classification Search
None
See application file for complete search history.

(56) References Cited

U.S. PATENT DOCUMENTS 5,827,641 A   10/1998 Parenteau et al.
6,080,579 A    6/2000 Hanley, Jr. et al.
2008/0081353 A1   4/2008 Islam et al.

OTHER PUBLICATIONS

Tang, Ming-Jer; et al; "Collagen gel overlay induces apoptosis of polarized cells in culture: disoriented cell death." American Journal of Physiology—Cell Physiology, 275, C921-C931, 1998.*
Jester, James V; Ho-Chang, Jin; "Modulation of cultured corneal keratocyte phenotype by growth factors/cytokines control in vitro contractility and extracellular matrix contractions." Experimental Eye Research, 77, 581-592, 2003.*
Duan, Derek; et al; "Progress in the development of a corneal replacement: keratoprostheses and tissue-engineered corneas." Expert Review of Medical Devices, 3, 59-72, 2006.*
Alaminos, Miguel; et al; "Construction of a Complete Rabbit Cornea Substitute Using a Fibrin-Agarose Scaffold" Investigative Ophthalmology & Visual Science, 47, 3311-3317, 2006.*
Birk et al. 1986. Organization of Collagen Types I and V in the Embryonic Chicken Cornea. Invest. Ophthalmol. Vis. Sci. vol. 27. pp. 1470-1477.
Birk et al. 1984. Extracellular Compartments in Matrix Morphogenesis: Collagen Fibril, Bundle, and Lamellar Formation by Corneal Fibroblasts. The Journal of Cell Biology. vol. 99. pp. 2024-2033.
Birk et al. 1981. Corneal and Scleral Collagen Fiber Formation in Vitro. Biochimica et Biophysica Acta. vol. 670. pp. 362-369.
Chaipinyo et al. 2002. "Effects of Growth Factors on Cell Proliferation and Matrix Synthesis of Low-Density, Primary Bovine Chondrocytes Cultured in Collagen I Gels." J. Orthop. Res. vol. 20. No. 5. pp. 1070-1078.
Bryant et al. 2002. "Hydrogel Properties Influence ECM Production by Chondrocytes Photoencapsulated in Poly (Ethyleneglycol) Hydrogels." J. Biomed. Mater. Res. vol. 59. pp. 63-72.
International Preliminary Report on Patentability for PCT application No. PCT/US2009/054899 dated Mar. 1, 2011.
Helseth et al. 1984. "Cathepsin D-Mediated Processing of Procollagen: Lysosomal Enzyme Involvement in Secretory Processing of Procollagen." Proceedings of the National Academy of Sciences of the United States of America. vol. 81. No. 11. pp. 3302-3306.
Parsons et al. 1999. "Mechanical Load Enhances Procollagen Processing in Dermal Fibroblasts by Regulating Levels of Procollagen C-Proteinase." Experimental Cell Research. vol. 252. pp. 319-331.
Atha et al. 1981. Mechanism of precipitation of proteins by polyethylene glycols. Analysis in terms of excluded volume. J. Biol. Chem. vol. 256. No. 23. pp. 12108-12117.
Bateman et al. 1987. Cell-layer-associated proteolytic cleavage of the telopeptides of type I collagen in fibroblast culture. Biochem. J. vol. 245. pp. 677-682.
Bateman et al. 1986. Induction of procollagen processing in fibroblast cultures by neutral polymers. J. Biol. Chem. vol. 261. No. 9. pp. 4198-4203.

(Continued)

*Primary Examiner* — Blaine Lankford, Jr.
*Assistant Examiner* — David Berke-Schlessel
(74) *Attorney, Agent, or Firm* — Michele L. Lawson; Michael M. McGaw; Smith & Hopen, P.A.

(57) ABSTRACT

A method of enhancing the formation of extracellular matrix in culture. Cells in culture secrete most of the collagen into the media as unprocessed procollagen, i.e., the cells do not convert procollagen to collagen. In contrast, normal extracellular matrix deposition involves procollagen processing to collagen, fibril assembly and deposition into the cell layer to form a collagenous extracellular matrix. The addition of certain growth factors and the addition of a thin layer of a certain volume exclusion agent on top of the cells dramatically enhances the conversion of procollagen to collagen and will increase the amount of collagen and extracellular matrix associated with the cells. This invention advances bioengineering of connective tissues for medical applications that require an extensive and functional extracellular matrix with high tensile strength such as those in the cornea stroma, skin, tendons, ligaments, articular cartilage and the intervertebral disks.

15 Claims, 11 Drawing Sheets

(56) References Cited

OTHER PUBLICATIONS

Beales et al. 1999. Proteoglycan synthesis by bovine keratocytes and corneal fibroblasts: maintenance of the keratocyte phenotype in culture. Invest. Ophthalmol. Vis. Sci. vol. 40. pp. 1658-1663.

Berryhill et al. 2001. Production of prostaglandin D synthase as a keratan sulfate proteoglycan by cultured bovine keratocytes. Invest. Ophthalmol. Vis. Sci. vol. 42. pp. 1201-1207.

Blochberger et al. 1992. cDNA to chick lumican (corneal keratan sulfate proteoglycan) reveals homology to the small interstitial proteoglycan gene family and expression in muscle and intestine. J. Biol. Chem. vol. 267. pp. 347-352.

Buschmann et al. 1992. Chondrocytes in agarose culture synthesize a mechanically functional extracellular matrix. J. Orthop. Res. vol. 10. pp. 745-758.

Canty et al. 2005. Procollagen trafficking, processing and fibrillogenesis. J. Cell. Sci. vol. 118. pp. 1341-1353.

Chakravarti et al. 1998. Lumican regulates collagen fibril assembly: skin fragility and corneal opacity in the absence of lumican. J. Cell. Biol. vol. 141. pp. 1277-1286.

Chakravarti et al. 2006. Collagen fibril assembly during postnatal development and dysfunctional regulation in the lumican-deficient murine cornea. Dev. Dyn. vol. 235. pp. 2493-2506.

Chang et al. 1997. Structural colocalisation of type VI collagen and fibronectin in agarose cultured chondrocytes and isolated chondrons extracted from adult canine tibial cartilage. J. Anat. vol. 190. Pt. 4. pp. 523-532.

Cintron et al. 1988. Heterogeneity of collagens in rabbit cornea: type VI collagen. Invest. Ophthalmol. Vis. Sci. vol. 29. No. 5. pp. 760-766.

Cintron et al. 1988. Heterogeneity of collagens in rabbit cornea: type III collagen. Invest. Ophthalmol. Vis. Sci. vol. 29. No. 5. pp. 767-775.

Corpuz et al. 1996. Molecular cloning and tissue distribution of keratocan. Bovine corneal keratan sulfate proteoglycan 37A. J. Biol. Chem. vol. 271. No. 16. pp. 9759-9763.

Dimicco et al. 2007. Structure of pericellular matrix around agarose-embedded chondrocytes. OsteoArthritis and Cartilage. vol. 15. pp. 1207-1216.

Foellmer et al. 1983. A monoclonal antibody specific for the amino terminal cleavage site of procollagen type I. Eur. J. Biochem. vol. 134. pp. 183-189.

Funderburgh et al. 1997. Mimecan, the 25-kDa corneal keratan sulfate proteoglycan, is a product of the gene producing osteoglycin. J. Biol. Chem. vol. 272. No. 44. pp. 28089-28095.

Goldberg et al. 1972. Precursors of collagen secreted by cultured human fibroblasts. Proc. Natl. Acad. Sci. USA. vol. 69. No. 12. pp. 3655-3659.

Govindraj et al. 2006. Modulation of FGF-2 binding to chondrocytes from the developing growth plate by perlecan. Matrix Biol. vol. 25. pp. 232-239.

Hassell et al. 2008. Increased stromal extracellular matrix synthesis and assembly by insulin activated bovine keratocytes cultured under agarose. Experimental Eye Research. vol. 87. pp. 604-611.

Hart et al. 2007. Thermally Associating Polypeptides Designed for Drug Delivery Produced by Genetically Engineered Cells. J. Phar.. Sci. vol. 96. pp. 484-516.

Jester et al. 2003. Modulation of cultured corneal keratocyte phenotype by growth factors/cytokines control in vitro contractility and extracellular matrix contraction. Exp. Eye Res. vol. 77. pp. 581-592.

Liu et al. 2003. Keratocan-deficient mice display alterations in corneal structure. J. Biol. Chem. vol. 278. No. 24. pp. 21672-21677.

Muller et al. 2001. The effects of organ-culture on the density of keratocytes and collagen fibers in human corneas. Cornea. vol. 20. No. 1. pp. 86-95.

Musselmann et al. 2005. Maintenance of the keratocyte phenotype during cell proliferation stimulated by insulin. J. Biol. Chem. vol. 280. No. 38. pp. 32634-32639.

Musselmann et al. 2006. Stimulation of collagen synthesis by insulin and proteoglycan accumulation by ascorbate in bovine keratocytes in vitro. Invest. Ophthalmol. Vis. Sci. vol. 47. pp. 5260-5266.

Musselmann et al. 2008. IGF-II is present in bovine corneal stroma and activates keratocytes to proliferate in vitro. Exp. Eye Res. vol. 86. pp. 506-511.

Oh et al. 1993. Tissue-specific expression of type XII collagen during mouse embryonic development. Dev. Dyn. vol. 196. pp. 37-46.

Rada et al. 1993. Regulation of corneal collagen fibrillogenesis in vitro by corneal proteoglycan (lumican and decorin) core proteins. Exp. Eye. Res. vol. 56. pp. 635-648.

Segev et al. 2006. Structural abnormalities of the cornea and lid resulting from collagen V mutations. Invest. Ophthalmol. Vis. Sci. vol. 47.No. 2. pp. 565-573.

Wenstrup et al. 2004. Type V collagen controls the initiation of collagen fibril assembly. J. Biol. Chem. vol. 279. No. 51. pp. 53331-53337.

Lareu et al. 2007. In vitro augmentation of collagen matrix formation—applications in tissue engineering. IFMBE Proceedings. vol. 15. pp. 696-699.

Li et al. 1992 cDNA clone to chick corneal chondroitin/dermatan sulfate proteoglycan reveals identity to decorin. Arch. Biochem. Biophys. vol. 296. No. 1. pp. 190-197.

Meek et al. 2003. An X-ray scattering investigation of corneal structure in keratocan-deficient mice. Matrix Biol. vol. 22. pp. 467-475.

Lelbach et al. 2005. The insulin-like growth factor system: IGFs, IGF-binding proteins and IGFBP-proteases. Acta Physiol. Hung. vol. 92. No. 2. pp. 97-107.

Jester et al. 1996. Induction of alpha-smooth muscle actin expression and myofibroblast transformation in cultured corneal keratocytes. Cornea vol. 15. No. 5. pp. 505-516.

Birk. 2001. Type V collagen: heterotypic type I/V collagen interactions in the regulation of fibril assembly. Micron. vol. 32. pp. 223-237.

Benya et al. 1982. Dedifferentiated chondrocytes reexpress the differentiated collagen phenotype when cultured in agarose gels. Cell. vol. 30. pp. 215-224.

Silver et al. 1983. Kinetic analysis of collagen fibrillogenesis: I. Use of turbidity-time data. Collagen. Rel. Res. vol. 3. pp. 393-405.

\* cited by examiner

VOLUME EXCLUSION AGENT TO ENHANCE FORMATION OF EXTRACELLULAR MATRIX

CROSS REFERENCE TO RELATED APPLICATIONS

This application is a continuation of prior filed International Application, Ser. No. PCT/US2009/054899 filed Aug. 25, 2009, which claims priority to U.S. provisional patent application No. 61/091,584 filed Aug. 25, 2008 which is hereby incorporated by reference into this disclosure.

STATEMENT OF GOVERNMENT INTEREST

This invention was made with Government support under Grant Nos. EY008104 and EY05129 awarded by the U.S. Department of Health and Human Services/National Institutes of Health. The Government has certain rights in the invention.

FIELD OF INVENTION

This invention relates to cell culture methodology. More specifically, this invention relates to enhanced formation of extracellular matrices using volume exclusion agents.

BACKGROUND OF THE INVENTION

Collagen is necessary for the tensile strength and structural integrity of tissues. Cells in culture make very low levels of collagen but can be stimulated to make higher levels of collagen, in the form of procollagen, by the addition of growth factors. Additionally, cells in culture do not efficiently process procollagen to collagen. As a result, even if collagen synthesis is stimulated, almost all of the procollagen is released into the media and little or no collagen is assembled into fibrils associated with the cells.

The corneal stroma of the eye contains an extensive and transparent extracellular matrix that is interspersed with keratocytes. Transparency of this matrix requires uniformly small diameter collagen fibrils with constant inter-fibril spacing. The matrix is composed primarily of the fibrillar collagen types I and V, with lesser amounts of types III, VI and XII, and four leucine-rich type proteoglycans; three with keratin sulfate chains, lumican, keratocan, and osteoglycin/mimecan, and one with a chondroitin sulfate chain, decorin. In vitro studies have shown that collagen type V and the core proteins of the leucine-rich proteoglycans can act to regulate collagen fibril growth and these findings have been confirmed in vivo in the Col5a1 haploinsufficent mouse, in the lumican null mouse and in the keratocan null mouse.

The keratocytes in the corneal stroma are responsible for making, maintaining and repairing the corneal stroma's matrix. Keratocytes can be isolated from the stroma of rabbit and bovine corneas by collagenase digestion. Once isolated, they can be cultured in serum free media where they maintain their normal dendritic morphology as well as other in vivo characteristics (Beales et al., Proteoglycan synthesis by bovine keratocytes and corneal fibroblasts: maintenance of the keratocyte phenotype in culture. Invest Ophthalmol Vis Sci (1999) 40:1658-1663). The media supplement "ITS" and high levels of insulin, a component of "ITS", have been shown to stimulate the proliferation of bovine keratocytes while maintaining their dendritic morphology and keratan sulfate proteoglycan synthesis (Musselmann K, et al., Maintenance of the keratocyte phenotype during cell proliferation stimulated by insulin. J Bio Chem (2005) 280:32634-32639). Furthermore, in the presence of ascorbic acid, a cofactor necessary for collagen triple helix stability, insulin also has been shown to increase the synthesis of collagen by 11-fold and lumican/keratocan by 2-3 fold (Musselmann et al., Stimulation of collagen synthesis by insulin and proteoglycan accumulation by ascorbate in bovine keratocytes in vitro. Invest Ophthalmol Vis Sci (2006) 47: 5260-5266). Thus, insulin may act to maintain the normal keratocyte phenotype and that proteoglycan stability may be linked to collagen stability.

Insulin has a high affinity for its own receptor, and it also has a low affinity for the IGF-I receptor. High levels of insulin would therefore activate keratocytes through both receptors. High levels of insulin would not normally be present in the corneal stroma, however IGF-II, another ligand for IGF-IR, is in the bovine corneal stroma and it causes bovine keratocytes to proliferate and maintain their normal phenotype in vitro (Musselmann et al., IGF-II is present in bovine corneal stroma and activates keratocytes to proliferate in vitro. Exp Eye Res (2008) 86:506-511). IGF-I stimulates the proliferation of rabbit keratocytes in vitro while maintaining their dendritic morphology.

As discussed above, even if collagen synthesis is stimulated using growth factors, almost all of the procollagen is released into the media and little or no collagen is assembled into fibrils associated with the cells. Improvements in the techniques used to facilitate matrix deposition and formation are desired in the art.

SUMMARY OF THE INVENTION

Cells in culture secrete most of the collagen into the media as unprocessed procollagen, i.e., the cells do not convert procollagen to collagen. In contrast, normal extracellular matrix deposition involves procollagen processing to collagen, fibril assembly and deposition into the cell layer to form a collagenous extracellular matrix. We have found that the addition of certain growth factors to the culture medium will stimulate collagen synthesis. We have also discovered that adding a thin layer of a certain volume exclusion agent on top of the cells will dramatically enhance the conversion of procollagen to collagen and will increase the amount of collagen and extracellular matrix associated with the cells. In addition, it is associated with a more normal cell topography associated with tissue-specific extracellular matrix assembly in vivo.

Cells in culture make very low levels of collagen but can be stimulated to make higher levels of collagen, in the form of procollagen, by the addition of the growth factors IGF-I, PDGF, TGF-β or insulin to the medium as taught herein. The effect of high levels of insulin and low levels of IGF-I on keratocyte proliferation and on the synthesis of collagen and proteoglycans by bovine keratocytes in culture is shown herein. The effect of an agarose overlay on the processing of procollagen to collagen required for fibril formation and extracellular matrix assembly is also detailed in the present disclosure.

This invention will be useful for the bioengineering of connective tissues for medical applications that require an extensive and functional extracellular matrix with high tensile strength such as those in the cornea stroma, skin, tendons, ligaments, articular cartilage and the intervertebral disks. In addition, a tissue-specific matrix would be essential as a scaffold for cells in applications where cell-matrix interactions are important to maintain cell phenotype and a tissue-specific matrix would facilitate integration with the surrounding extracellular matrix into which it was implanted, e.g., an artificial pancreas.

In a first aspect this invention provides a method of enhancing the formation of extracellular matrices in culture. The method includes the steps of plating out cells on a tissue culture substrate, adding a volume exclusion agent on top of the plated cells, adding tissue culture media containing a growth factor to the substrate containing the overlaid plated cells, and incubating the plated cells in a tissue culture incubator. The growth factor can be IGF-I, PDGF, TGF-β or insulin. A hydrogel can be used as the volume exclusion agent. Advantageous hydrogels include agarose, kappa-carrageenan, iota-carrageenan, gelatin, elastin-mimetic protein polymers and silk-elastin block copolymers. Dialysis membranes with predetermined MW pore sizes and high viscosity solutions of methylcellulose can also be used as the volume exclusion agent. Pore sizes of the membranes can be selected based upon the desired retention or diffusion characteristics of the membrane relative to the secreted molecules. For example, if one seeks to retain a secreted protein within the environment created by the membrane, a membrane could be selected with a pore size sufficiently small to ensure that the molecule is unable to diffuse across the barrier created by the membrane. In light of the foregoing, membranes having pore sizes of 10 kd, 13 kd, 25 kd, 50 kd to as large as 300 kd can be selected for use. Advantageously, a membrane of about 25,000 to 50,000 MW pore size is employed. Agarose overlays are particularly advantageous volume exclusion agents. Agarose overlays can be made from an approximately 3% solution of low melting temperature agarose in distilled water. Alternatively, the solution of low melting temperature agarose can be an approximately 1%, 2%, 4%, 5%, or 6% solution, or in a range from 1-6%, 2-5%, 2-4%, 2.5-3.5%, or ranges encompassed therein. More particularly, the approximately 3% solution of low melting temperature agarose in distilled water can be prepared by combining an approximately 6% solution of low melting temperature agarose in distilled water with an equal volume of 2× tissue culture media containing 2× growth factor. The method of enhancing the formation of extracellular matrices in culture can further include the steps of adding media containing a growth factor to the plated cells following the plating of the cells on a tissue culture substrate, incubating the plated cells to facilitate attachment of the cells to the tissue culture substrate and removing the media from the substrate containing the growth factor stimulated cells. The cells can be incubated for a period of 1-4 days to allow for attachment. Advantageously, the incubation to allow for attachment is about four days before the agarose overlay is added. Moreover, the cells can be plated at a high density of about 100,000-cells/cm2. Alternatively, the density can be in the range of 50,000-150,000-cells/cm2, 60,000-140,000-cells/cm2, 75,000-125,000-cells/cm2, or 80,000-120,000-cells/cm2. In an advantageous embodiment the cells are fibroblasts. In a particularly advantageous embodiment the cells are keratocytes, tenocytes or chondrocytes.

In a second aspect this invention provides a method of enhancing the formation of extracellular collagen matrices in culture. The method includes the steps of plating out keratocytes on a tissue culture substrate, adding a volume exclusion agent on top of the plated keratocytes, adding tissue culture media containing a growth factor to the substrate containing the overlaid plated cells and incubating the plated keratocytes in a tissue culture incubator. The growth factor can be IGF-I or insulin. A hydrogel can be used as the volume exclusion agent. Advantageous hydrogels include agarose, kappa-carrageenan, iota-carrageenan, gelatin, elastin-mimetic protein polymers and silk-elastin block copolymers. Agaose overlays are particularly advantageous volume exclusion agents.

In a third aspect this invention provides a second method of enhancing the formation of extracellular matrices. The method includes the steps of plating out cells on a tissue culture substrate, adding a hydrogel overlay on top of the plated cells, adding tissue culture media containing a growth factor to the substrate containing the overlaid plated cells and incubating the plated cells in a tissue culture incubator. Advantageous hydrogels include agarose, kappa-carrageenan, iota-carrageenan, gelatin, elastin-mimetic protein polymers and silk-elastin block copolymers. In an advantageous embodiment the cells are fibroblasts. In a particularly advantageous embodiment the cells are keratocytes.

This invention enhances both the synthesis of collagen and the conversion of procollagen to collagen and, as a result, increases extra cellular matrix formation associated with the cells. This invention will now make it possible to bioengineer tissues with high tensile strength and structural integrity.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
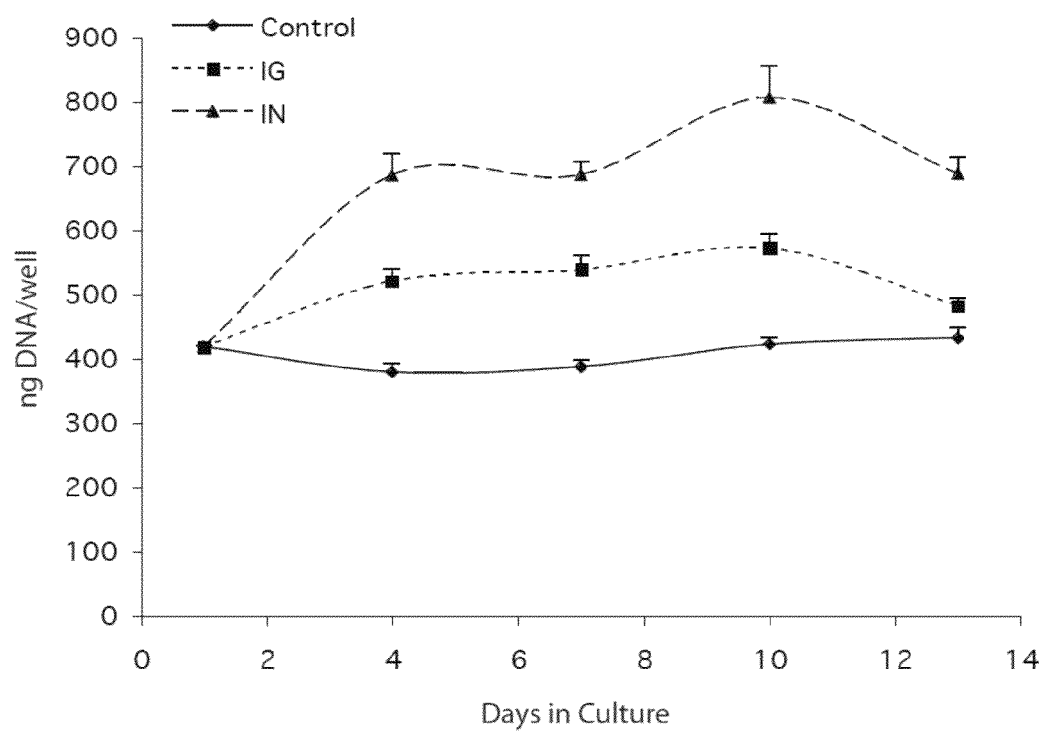
FIG. 1 shows the DNA content of keratocyte cultures. Keratocytes were cultured in media alone (Control/diamonds) or in media containing either IGF-I (IG/squares) or insulin (IN/triangles) and harvested on day 1, 4, 7, 10, and 13 of culture. Compared to control, cultures in media containing IGF-I or insulin contained significantly more DNA at the $p<0.016$ and $p<0.005$ levels respectively, for all time points.

Cells in culture secrete most of the collagen into the media as unprocessed procollagen. In other words, the cells do not convert the procollagen to collagen. In contrast, normal extracellular matrix deposition involves procollagen processing to collagen, fibril assembly and deposition into the cell layer to form a collagenous extracellular matrix. We have found that the addition of certain growth factors to the culture medium will stimulate collagen synthesis. We have also discovered that adding a thin layer of a certain volume exclusion agent on top of the cells will dramatically enhance the conversion of procollagen to collagen and will increase the amount of collagen and extracellular matrix associated with the cells. In addition, it is associated with a more normal cell topography associated with tissue-specific extracellular matrix assembly in vivo. This invention will be useful for the bioengineering of connective tissues for medical applications that require an extensive and functional extracellular matrix with high tensile strength such as those in the cornea stroma, skin, tendons, ligaments, articular cartilage and the intervertebral disks. In addition, a tissue-specific matrix would be essential as a scaffold for cells in applications where cell-matrix interactions are important to maintain cell phenotype and a tissue-specific matrix would facilitate integration with the surrounding extracellular matrix into which it was implanted, e.g., an artificial pancreas.

As used herein, a "volume exclusion agent" is a semipermeable barrier or membrane used to overlay cells where the barrier or membrane keeps the procollagen secreted from the cells at or near the keratocyte surface. By keeping the procollgen at or near the surface, while similarly impeding the diffusion of necessary enzymes to convert procollagen to collagen, the volume exclusion agent effects the efficient processing of procollagen to collagen and assists in the subsequent fibril and matrix assembly.

Hydogels are advantageous volume exclusion agents. Hydrogels are hydrated polymer gels exhibiting a degree of flexibility similar to natural tissue. The hydrogel of the present invention may be produced from a hydrogel precursor selected from the group consisting of thermally gelling polysaccharides, such as agarose, or thermally gelling proteins, such as gelatin. Agarose is a natural polymer extracted from seaweed, and varies in its properties (molecular weight, precise chemical composition, side chains, etc.) and may be chemically functionalized to alter desirable properties such as the gelation temperature. Further, while commercially available agarose gels have a variety of electroendoosmosis (EEO) values when used for electrophoresis, such properties should not be critical in the present invention. Other potentially useful thermally gelling polysaccharides include kappa-carrageenan and iota-carrageenan. Gelatin is a protein derived from collagen from a wide variety of animal tissues and species. Like agarose, the properties of gelatin such as molecular weight and precise chemical composition are variable, yet the invention is not strongly dependent upon the exact compositions. Furthermore, there are other thermally gelling proteins that are potentially useful in this invention, such as elastin-mimetic protein polymers and silk-elastin block copolymers. See Hurt and Gehrke, Thermally Associating Polypeptides Designed for Drug Delivery Produced by Genetically Engineered Cells, J. Phar. Sci. Vol. 96 No. 3 (March 2007. In general, an elastin mimetic protein is one which has an amino acid sequence and secondary structure derived from native (naturally occurring) elastin.

The agarose or gelatin will preferably have a gelling temperature such that cells may be overlayed with a solution of the agarose or gelatin at a temperature that does not significantly impair cell viability. As such, the agarose or gelatin preferably does not gel at a temperature higher than that which is compatible with cell viability. Typically, for example, the agarose or gelatin should permit overlay at a temperature ranging from about 30° C. to 40° C. The solution preferably gels in less than about four hours, more preferably less than one hour, and still most preferably on the order of minutes (typically 1 to 20 minutes, and even 2 to 5 minutes). The solution also preferably takes more than one minute to gel so that there is sufficient time to overlay the cells on the tissue culture substrate. The actual gel point temperature is not critical if the gelation is sufficiently slow and as long as the gel is stable at the temperature range of the application and which preserves cell viability. Most preferred agarose gels are the so-called "low-melting" gels as they have gelation temperatures near 32° C. Thus, with such gels, there is less concern about inadvertently contacting the cells with a pre-gel solution that is too hot or that gels before the cells are fully dispersed in the solution.

As used herein, a "growth factor" is a naturally occurring substance capable of stimulating cell growth, proliferation and/or cellular differentiation. Growth factors are often a protein or a steroid hormone.

Pharmacological levels of insulin can stimulate the synthesis of normal corneal stromal collagen and proteoglycans by bovine keratocytes in culture. Insulin was compared to physiological levels of IGF-I and it was found that IGF-I also stimulated the synthesis of these extracellular matrix components, but less than that of insulin. Keratocytes in monolayer culture secreted most of the collagen synthesized into the media in the form of procollagen, a precursor of collagen. An overlay of 3% agarose on the keratocytes in culture was found to enhance the conversion of procollagen to collagen and increased the deposition of collagen and proteoglycans into the cell layer. The extracellular matrix associated with the keratocytes cultured under agarose exhibited a corneal stromal-like architecture. These results suggest that enhancing the conversion of procollagen to collagen is a key step in the formation of extracellular matrix by keratocytes in vitro. Agarose overlay of insulin-activated keratocytes in culture is a useful model for studying corneal stromal extracellular matrix assembly in vitro.

Example 1

Extracellular Matrix Formation by Keratocytes Cultures Under Agarose

Summary.

Ultrastructural analyses of the cell cultures demonstrated that the agarose overlay significantly enhanced the deposition of an extensive and normal appearing extracellular matrix. The matrix was characterized by collagen fibrils in the overlaid cultures which were sparse in the non-overlaid controls. This indicates normal processing of procollagen associated with fibril assembly. In addition, the overlay was associated with cell surface specializations/compartments characteristic of cells in vivo. These microdomains are associated with fibril and matrix deposition and not present in the non-over-laid cultures.

We have found that the addition of certain growth factors to the culture medium will stimulate collagen synthesis. We have also discovered that adding a thin layer of a certain volume exclusion agent on top of the cells will dramatically enhance the conversion of procollagen to collagen and will increase the amount of collagen and extracellular matrix associated with the cells. In addition, it is associated with a more normal cell topography associated with tissue-specific extracellular matrix assembly in vivo.

The ability of insulin and IGF-1 to stimulate the proliferation of keratocytes in culture was evaluated over a 13-day period. Keratocytes were isolated from corneas and plated in DMEM/F12 on the same day. The media was changed the following day (day 1) to media supplemented with 10 μg insulin/ml, 10 ng IGF-1/ml or unsupplemented media (control) and the DNA content of the cultures was determined on days 1, 4, 7, 10, and 13 of culture. Compared to controls, cultures supplemented with insulin or with IGF-1 contained significantly higher levels of DNA by day 4 of culture and essentially remained at those levels for the duration of the culture period (FIG. 1).

Figure 2:
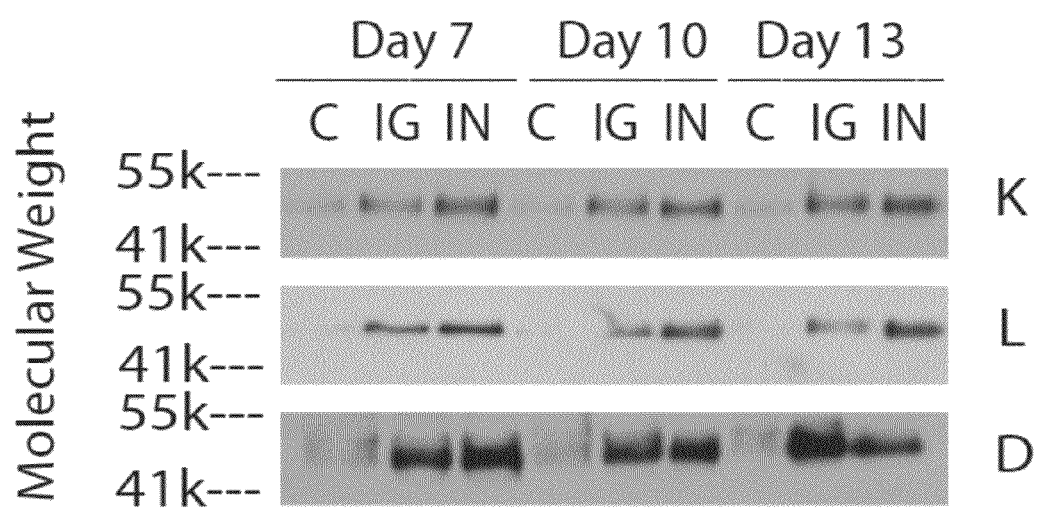
FIG. 2 shows SDS/PAGE/Western blot of media from keratocyte cultures using antibodies to keratocan (K), lumican (L), and decorin (D). Keratocytes were cultured in media alone (C) or in media containing either IGF-I (IG) or insulin (IN). Media was harvested on days 7, 10, and 13 and then digested with either endo-β-galactosidase, for lumican and keratocan, or chondroinase ABC, for decorin, prior to electrophoresis.

Media from these cultures was changed every 3 days. The media harvested on days 7, 10, and 13 of culture was digested either with endo-β-galactosidase or with chondroitinase ABC and was evaluated either for keratocan and lumican content or for decorin content, respectively, by western blot using antibodies to the core proteins of these proteoglycans. The volume of media analyzed was normalized to the DNA content. The media from the IGF-1 cultures contained substantially higher levels of these proteoglycans than media from control cultures and, in most instances, the media from the insulin cultures contained even higher levels than the media from IGF-1 cultures (FIG. 2).

Figure 3:
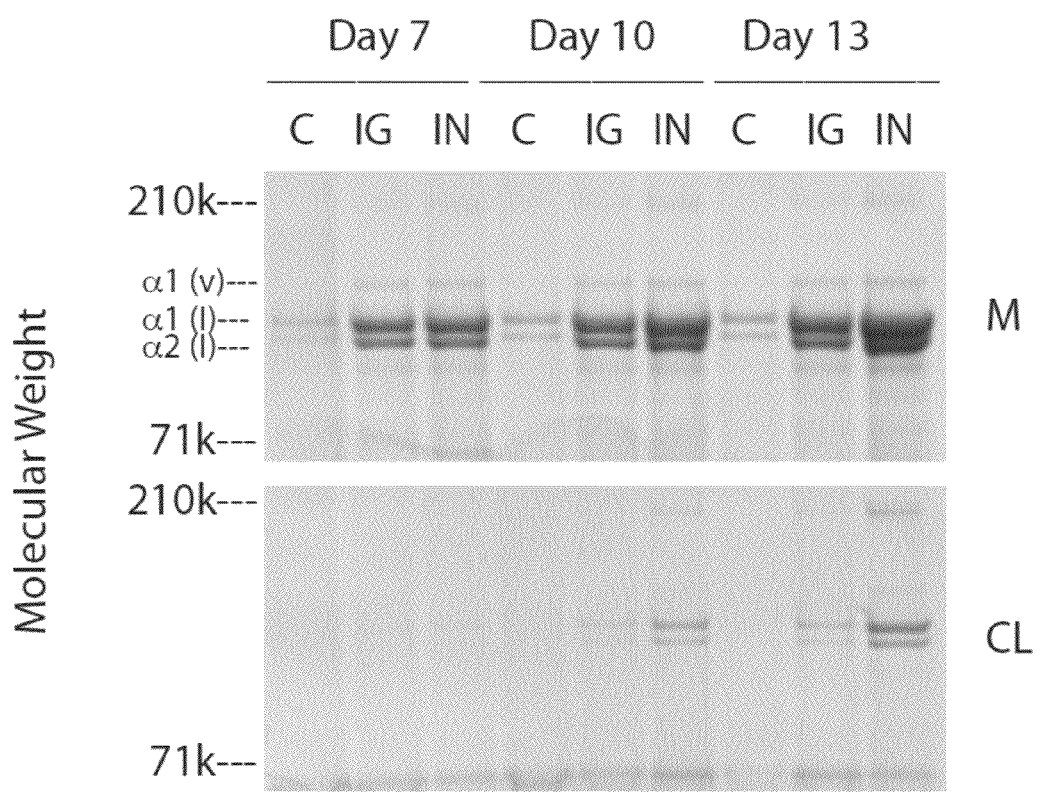
FIG. 3 shows SDS/PAGE/Blue stain of pepsin digests from keratocyte cultures. Keratocytes were cultured in media alone (C) or in media containing either IGF-I (IG) or insulin (IN). Cultures were harvested on day 7, 10, and 13. The media (M) and cell layers (CL) were digested with pepsin prior to electrophoresis.

Pepsin readily degrades globular proteins, but the triple helical domains of collagen are resistant to this protease. Aliquots of pepsin digested media and cell layers, normalized for DNA, harvested from the day 7, 10, and 13 time points were fractionated on SDS/PAGE and the collagenous proteins visualized by simply blue staining (FIG. 3). Similar to that seen for the proteoglycans, the media (M) from the IGF-1 cultures contained substantially higher amounts of the α1(I), α2(I) and α1(V) chains of collagen than the control cultures and media from the days 10 and 13 insulin cultures contained slightly higher levels of these collagens than the IGF-1 cultures. Collagenous protein was not detected in the cell layer (CL) until day 10 and there was considerably less collagenous protein in the cell layer compared to that in the media, but by day 13 the same trend seen in the media was apparent in the cell layer: that is, more collagen in the IGF-1 cultures than controls and even more in the insulin cultures. These results demonstrate that most of the collagenous proteins synthesized were deposited in the media.

Figure 4:
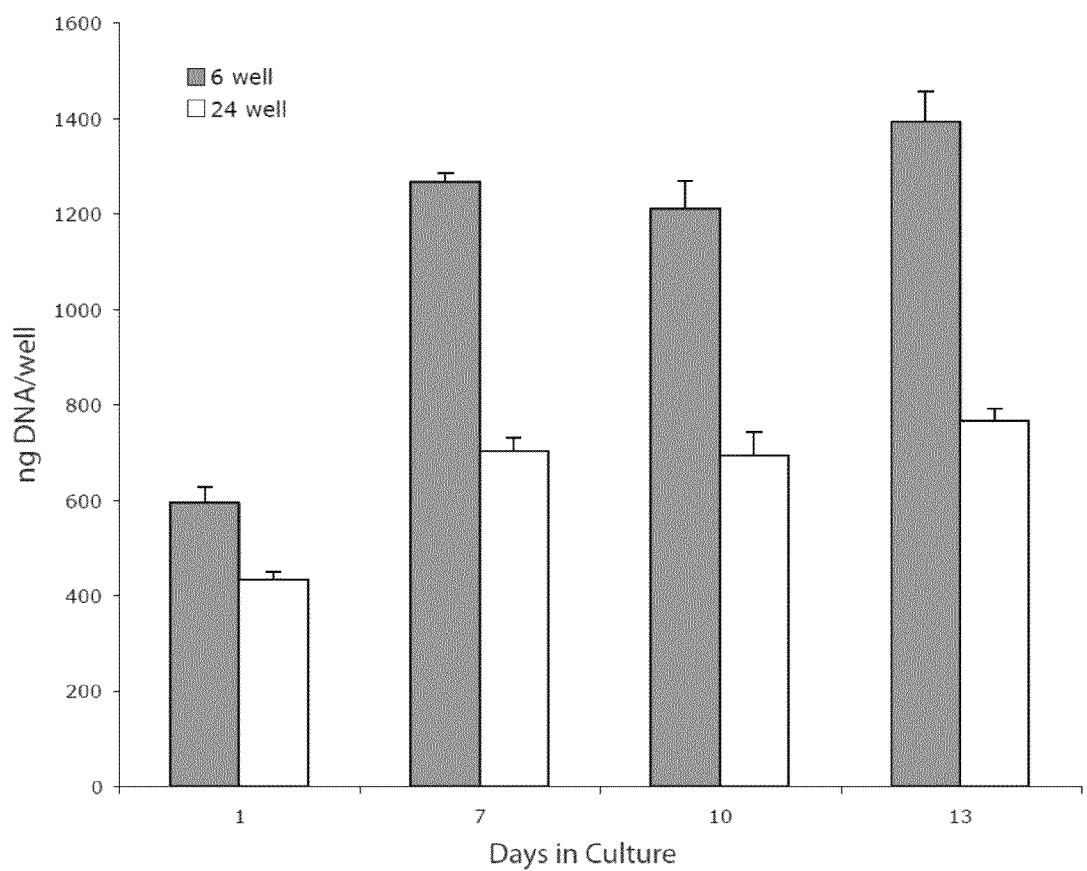
FIG. 4 shows the DNA content of keratocyte cultures. Keratocytes were plated at low density (6 well) or high density (24 well), cultured in media containing insulin starting on day 1 and harvested on days 1, 7, 10, and 13. Compared to day 1 cultures, the DNA content of cultures significantly increased for all subsequent time points whether plated at low density ($p<0.016$) or high density ($p<0.003$).
Figure 5:
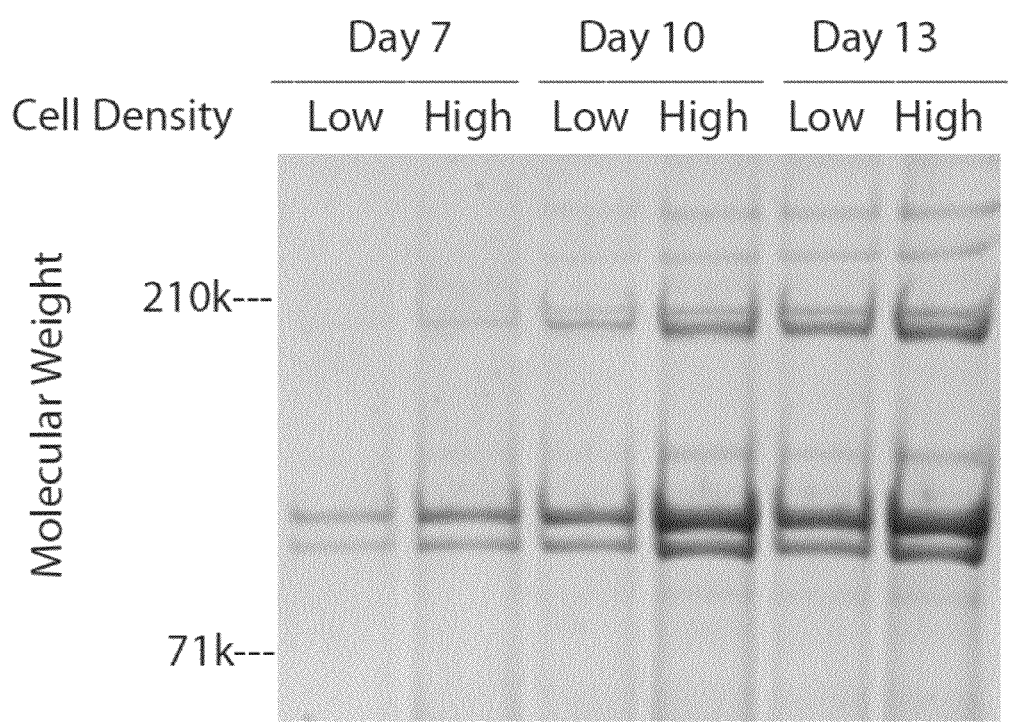
FIG. 5 shows SDS/PAGE/Blue stain of pepsin digested cell layers from keratocyte cultures. Keratocytes were plated at low density (Low) or high density (High), cultured in media containing insulin and harvested on days 7, 10, and 13. The cell layers were digested with pepsin prior to electrophoresis.

We next determined if deposition of collagen with the cell layer could be enhanced by plating keratocytes at a higher density. The same number of cells (400,000) were plated per well in 6 and in 24 well plates to produce a five-fold difference in plating density; ~20,000-cells/cm2 in 6 well plates (low density cultures) and ~100,000 cells/cm2 in 24 well plates (high density cultures). It was possible, however, to use the same amount (2 mls) of media per well during subsequent culture for both cell densities because of the depth of the wells. One day after plating (day 1), there was 27% less DNA/well in the high density cultures than in the low density cultures which suggests that keratocytes may have higher attachment efficiencies at the lower plating density (FIG. 4). The DNA content per well increased significantly during the subsequent 12 days of culture in both plates; ~2.1 fold increase in the low density cultures and ~1.7 fold increase in the high density cultures. Thus, during days 7-10 of culture, the cell density in the high density cultures was only ~2.6 fold higher than in the low density cultures. SDS/PAGE analyses of aliquots of pepsin digests from the cell layers, normalized to DNA content, demonstrated that the levels of collagenous proteins were slightly greater in cells at the higher density at all 3 time points (FIG. 5).

Figure 6:
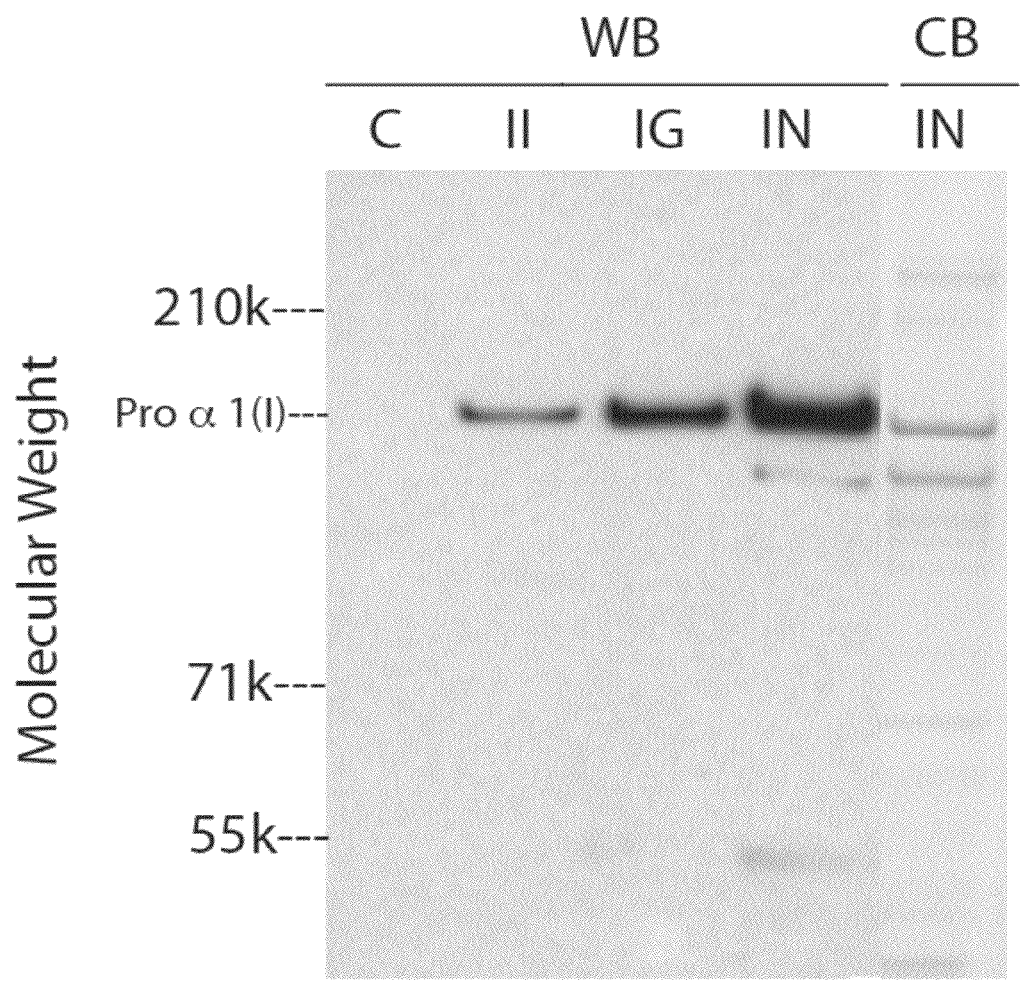
FIG. 6 shows SDS/PAGE of media from keratocyte cultures. Keratocytes were cultured in media alone (C) or in media containing IGF-II (II), IGF-I (IG) or insulin (IN) and cultures were harvested on day 10. SDS/PAGE gels of the media were examined by Western blots with an antibody to procollagen type I (WB) or stained directly with blue stain (CB).

Type I collagen is initially synthesized as procollagen with N– and C– terminal globular domains. The procollagen globular domains are cleaved by specific proteases during post-translational processing and this allows the triple helical regions of collagen to laterally associate into fibrils. The processing of type I procollagen and subsequent assembly of collagen fibrils occurs quickly and completely in vivo. In contrast, cultured fibroblasts incompletely process procollagen to collagen and because procollagen cannot efficiently form normal fibrils, it accumulates in the culture medium (Goldberg et al., Precursors of collagen secreted by cultured human fibroblasts. Proc Natl Acad Sci USA (1972) 69:3655-3659). Consequently, we analyzed culture medium, normalized for DNA, from keratocytes harvested on day 10 for type I procollagen using a monoclonal antibody (Foellmer et al., A monoclonal antibody specific for the amino terminal cleavage site of procollagen type 1. Eur J Biochem (1983)134:183-189) specific for the N-terminal globular domain of α1(I) by western blot (FIG. 6, lanes WB). Compared to controls, media from IGF-II cultures contained higher levels of type I procollagen. Furthermore, media from IGF-1 cultures and from insulin cultures contained increasingly higher levels of type I procollagen, respectively. Staining SDS/PAGE of media from insulin cultures for protein showed that the major protein band in the media co-migrated with the major band detected by the antibody to the pro-α1(I) (FIG. 6, lane CB).

Figure 7:
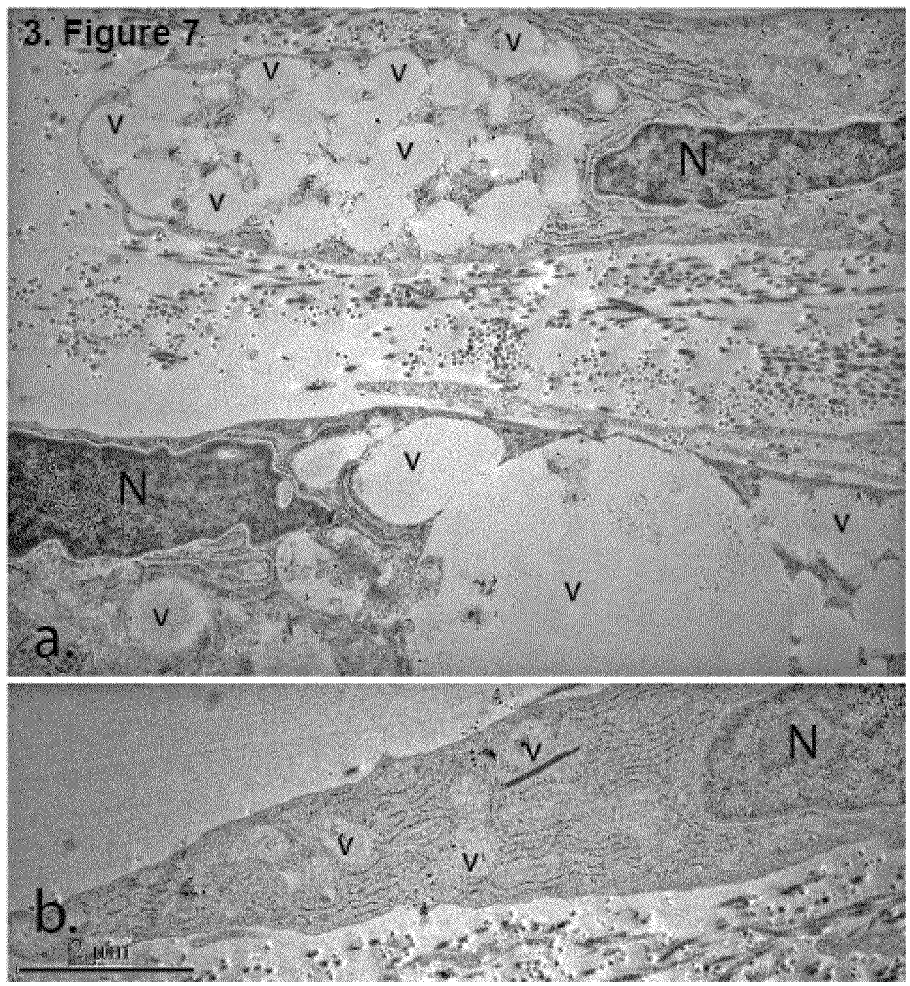
FIG. 7 shows transmission electron micrographs of day 13 cultures treated with and without dextran. Large clusters of cytoplasmic vacuoles (v) were a characteristic feature of the dextran-treated cultures (a). The untreated cultures (b) contained occasional cytoplasmic vacuoles (v). (N) Keratocyte nucleus; (v) cytoplasmic vacuoles.

The addition of neutral polymers, such as dextran and polyethylene glycol, to the culture medium has been shown to increase the processing of procollagen to collagen by fibroblasts in culture and to cause an increase in the amount of collagen associated with the cell layer (Bateman et al., Induction of pro collagen processing in fibroblast cultures by neutral polymers. J Biol Chem (1986) 261:4198-4203; Bateman et al., Cell-layer-associated proteolytic cleavage of the telopeptides of type I collagen in fibroblast culture. Biochem J (1987) 245: 677-682). We cultured insulin activated keratocytes in media supplemented with 5% dextran 40 and found that they deposited substantially lower levels of procollagen in the media and demonstrated increased levels of collagen associated with the cell layer (data not shown). However, the dextran treated keratocytes contained numerous large cytoplasmic vacuoles that were the predominant cytoplasmic feature (FIG. 7a). These vacuoles were large and found in large clusters. In contrast, the keratocytes cultured in the absence of dextran contained occasional vacuoles (FIG. 7b). Organ culture of human corneas in media containing dextran also has been shown to produce vacuoles in keratocytes. However, these vacuoles were comparable in size, morphology and distribution to those seen in the untreated control keratocytes.

Encapsulation of collagenase isolated chondrocytes by suspension in media containing 2% agarose has been shown to enhance the deposition of pericellular matrix by the chondrocyte during subsequent culture (Chang et al., Structural colocalisation of type VI collagen and fibronectin in agarose cultured chondrocytes and isolated chondrons extracted from adult canine tibial cartilage. J Anat (2007) 190 (Pt 4): 523-532). The pericellular matrix of chondrocytes contains collagen. We hypothesized that culture of keratocytes in agarose would enhance procollagen processing and deposition in the cell layer. However, instead of encapsulation, keratocytes were first plated at high density (100,000-cells/cm2), cultured in media containing insulin for days 1-4 and then, on day 4 of culture, the media was removed and media containing molten 3% agarose was layered on top of the attached cell layer. After the agarose has set, 2 mls of media was added to the well above the agarose layer. Cultures were harvested on days 7, 10, and 13 of culture without intervening media replacement.

Figure 8:
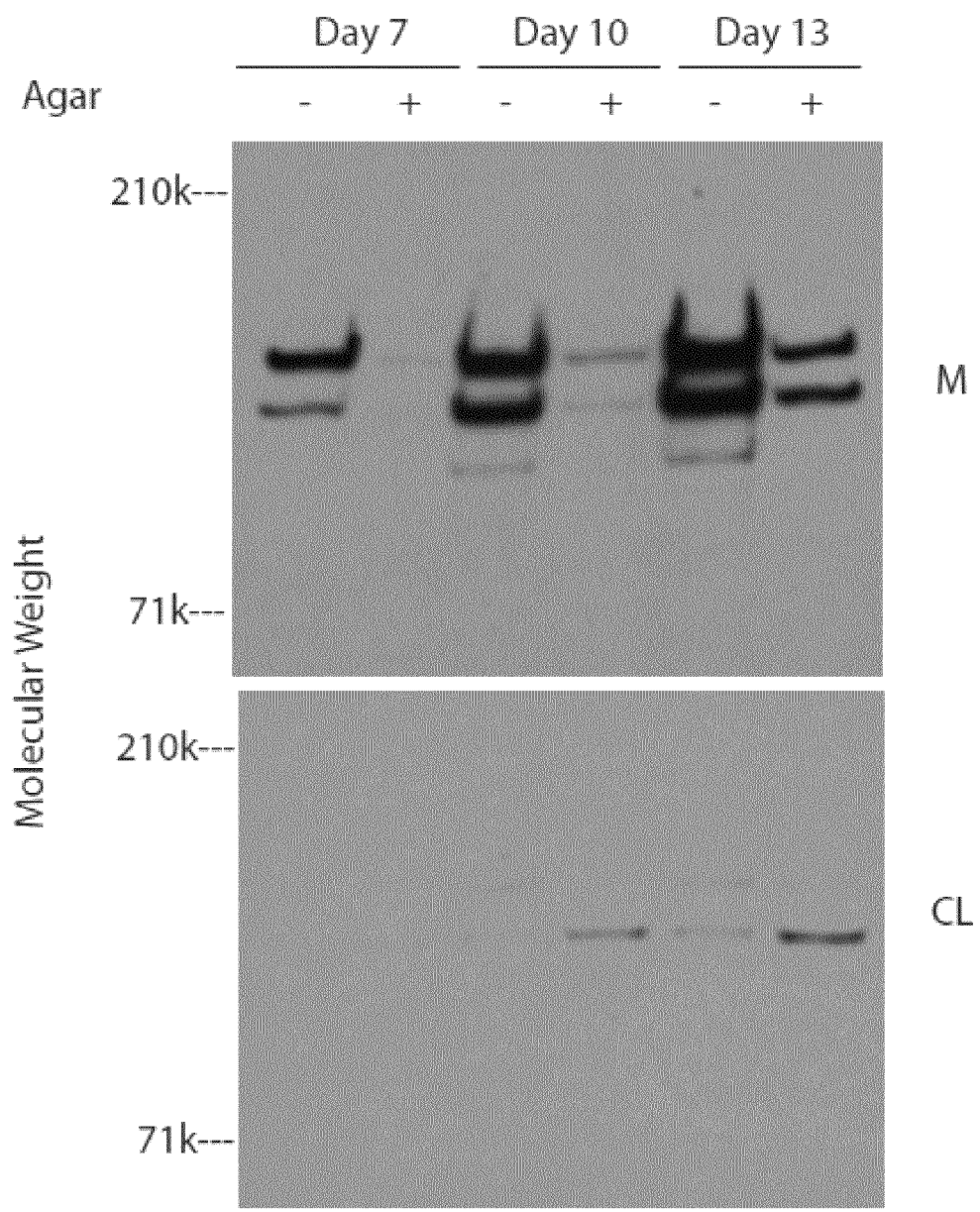
FIG. 8 shows SDS/PAGE/western blots using antibodies to procollagen type I. Keratocytes were cultured in media containing insulin and were either over-layered with agarose (+) or were not (−). Cultures were harvested on days 7, 10 and 13. The media (M) and extracts of the cell layers (CL) from the cultures were evaluated for procollagen type I content by Western blot.
Figure 9:
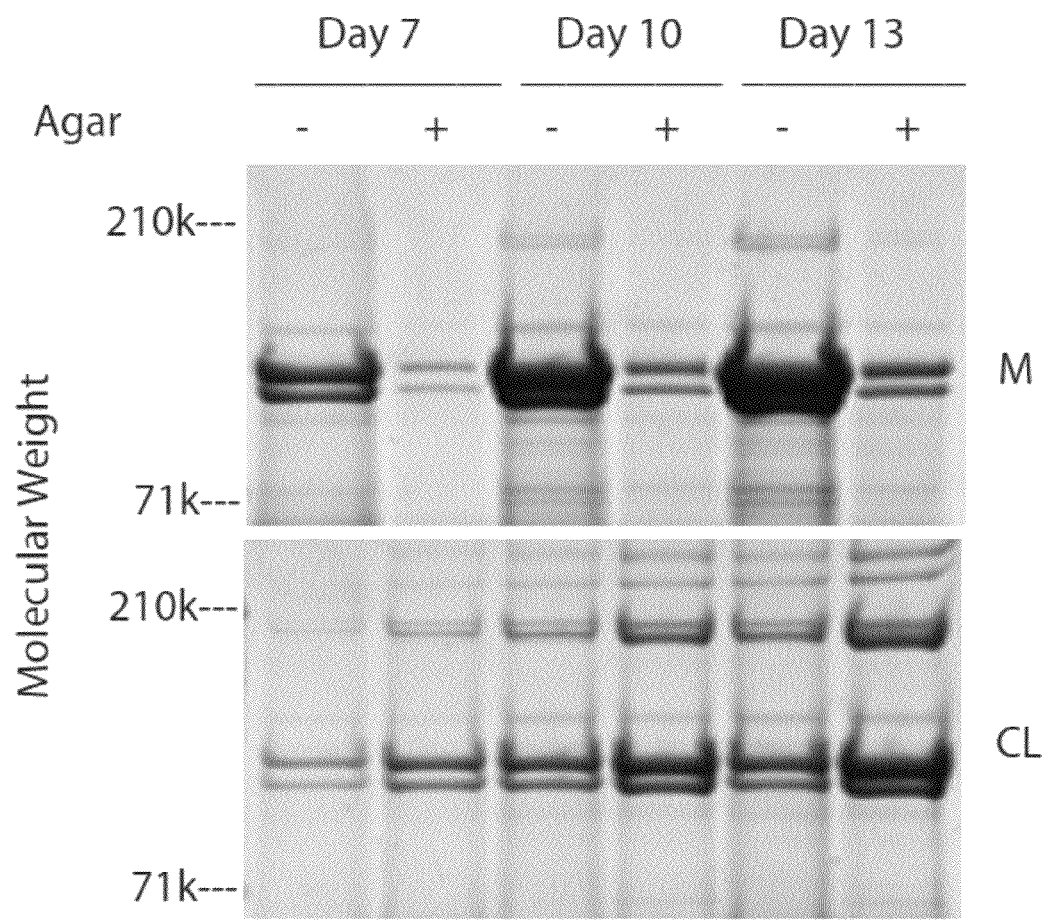
FIG. 9 shows SDS/PAGE/Blue stain of pepsin digests of keratocyte cultures. Keratocytes were cultured in media containing insulin and were either overlayed with agarose (+) or were not (−). Cultures were harvested on days 7, 10, and 13. The media and cell layers were digested with pepsin prior to electrophoresis.

Cultures with and without an agarose overlay were evaluated for collagen content in the two different compartments. SDS/PAGE/Western blots with antibodies to procollagen type I, of DNA-normalized aliquots from the media and acetic acid extracts of the cell layers showed that the media of agarose over-layered cultures contained substantially less procollagen type I than the media of cultures without agarose (FIG. 8). In contrast, the levels of type I procollagen in the cell layer extracts were far less than that in the media, although the extracts of cell layers over-layered with agarose contained higher levels of type I procollagen than the extracts of cell layers without agarose. SDS/PAGE analysis of DNA-normalized aliquots of pepsin digests of media and cell layers showed that compared to cultures without agarose, the agarose over-layered cultures contained substantially less collagenous protein in the media and also contained more collagenous protein in the cell layer at all 3 time points (FIG. 9). Together, the results in FIGS. 8 and 9 indicate that the collagenous proteins detected in the media are procollagen while the collagenous proteins detected in the cell layer are collagen. These results also indicate that the agarose overlay enhances the processing of procollagen to collagen resulting in fibril formation and association with the cell layer.

Figure 10:
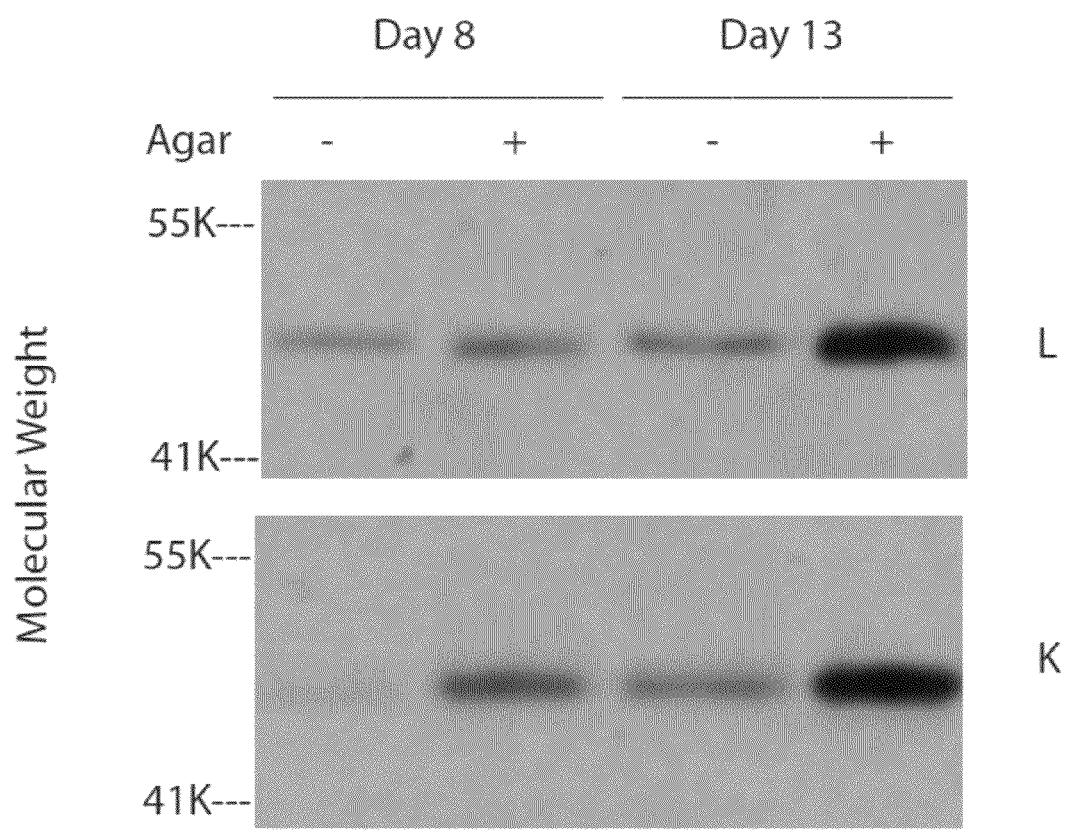
FIG. 10 shows SDS/PAGE/Western blots of cell layer extracts of keratocyte cultures using antibodies to lumican (L) and keratocan (K). Keratocytes were cultured in media containing insulin and were either overlayered with agarose (+) or were not (−). Cultures were harvested on days 8 and 13. Cell layer extracts were digested with endo-β--galactosidase prior to electrophoresis

Cultures with and without an agarose overlay were harvested on days 8 and 13 and guanidine extracts of the cell layers were evaluated for lumican and keratocan content. DNA-normalized aliquots of the extracts were digested with endo-β-galactosidase and core protein levels were determined by western blot using antibodies to lumican and keratocan (FIG. 10). Compared to cultures without agarose, cultures with agarose contained higher levels of lumican on day 13 and higher levels of keratocan on both days 8 and 13. These data indicate that the agarose overlay also enhances the incorporation of proteoglycans into the extracellular matrix.

Figure 11:
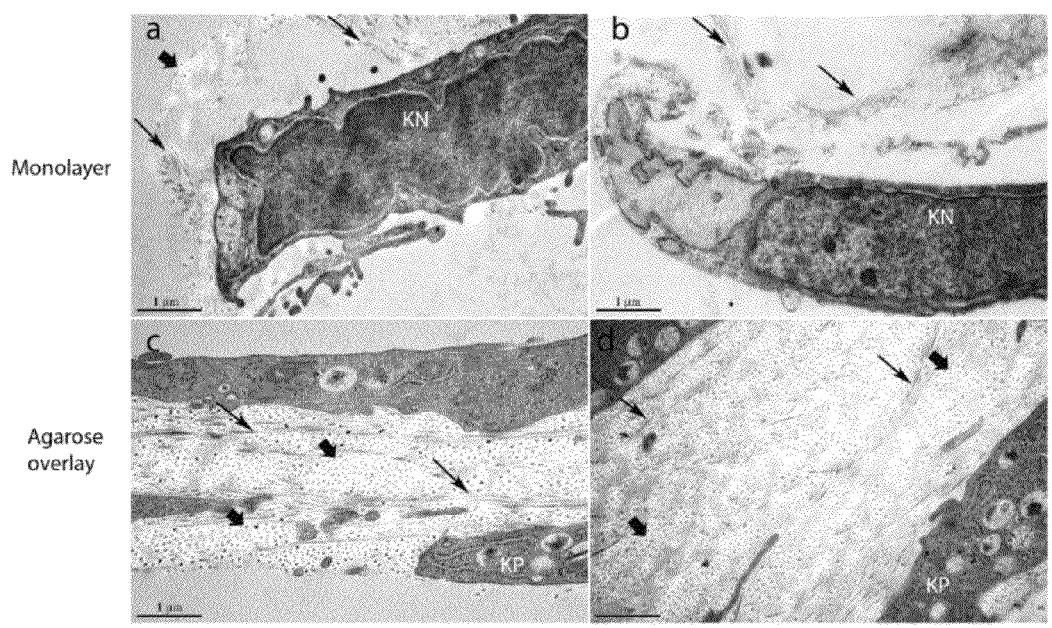
FIG. 11 shows transmission electron micrographs of day 13 cultures with and without an agarose overlay. Keratocytes were grown without agarose (a, b) or overlayed with agarose (c, d). Normal processing of procollagen in agarose overlay cultures results in corneal stroma-like matrix deposition. Keratocytes without agarose form monolayers with isolated collagen fibrils or small groups of fibrils (arrows). These are observed primarily associated with the keratocyte cell body. Keratocytes grown with an agarose overlay demonstrate stratification and the development of intercellular spaces defined by a series of complex cell processes. Keratocytes formed 2-4 layers separating lamellae-like structures containing abundant organized collagen fibrils. These spaces are filled with collagen fibrils that have small homogenous diameters and regular packing like that seen in the corneal stroma. The collagen fibrils are in both cross (wide arrows) and longitudinal (narrows arrows) comparable to that seen in the orthogonal stromal lamellae. Keratocytes without an agarose overlay appeared as sparse monolayers consistent with a dendritic morphology but with little matrix deposition and no stratification. (KN) keratocyte nucleus; (KP) keratocyte process.

Cultured keratocytes both with and without an agarose overlay were fixed at day 13 for transmission electron microscopy (FIG. 11). The keratocytes without an agarose overlay were arranged as monolayers. Keratocytes were associated with single and small groups of collagen fibrils. In contrast, the keratocyte cultures with the agarose overlay had a significant enhancement of collagen fibril deposition and also demonstrated stratification of the keratocytes. This was a major feature in large regions of the cultures with 2-4 layers of keratocytes. The regional nature coupled with the absence of keratocyte proliferation suggests the stratification resulted from reorganization and migration of keratocytes in response to the extracellular matrix deposited in the agarose overlay cultures. In addition, these cultures exhibited a more complex arrangement of keratocytes. The cells formed parallel spaced layers with numerous cytoplasmic processes delineating intercellular spaces. These spaces were filled with collagen fibrils displaying an orderly deposition of fibrils mimicking the cornea stroma-specific architecture, i.e., homogeneous small diameter fibrils with regular packing.

Pharmacological levels of insulin and physiological levels of IGF-I are shown herein to stimulate similar levels of cell proliferation, proteoglycan production and collagen synthesis by keratocytes in culture. The stimulation by insulin was, in most cases, slightly more than that of IGF-I. Insulin can bind to the receptors for IGF-I, but with much lower affinity. This suggests that the major pharmacological action of insulin could be through IGF-IR, but because the stimulation by insulin was greater than IGF-I, there may be additional actions of high levels of insulin on keratocytes, such as also activating the receptors for insulin. These data also indicate that, like shown for pharmacological levels of insulin, physiological levels of IGF-I can stimulate proliferation and the synthesis of normal matrix components by keratocytes.

While insulin substantially increased collagen synthesis by keratocytes, very little of the collagen made was deposited with the cell layer, i.e., assembled into fibrils. Increasing the length of time in culture and the initial plating density of the cells did, however, increase deposition of collagen with the cell layer. Most of the collagen was secreted into the media as procollagen, a precursor of collagen. The processing of procollagen to collagen by fibroblasts in culture was shown to be incomplete (Goldberg et al. 1972) and it is now apparent, from the data presented in this report, that keratocytes in culture also have this deficiency. We found, however, that culturing keratocytes under a layer of agarose enhanced the processing of procollagen to collagen, the assembly of collagen into fibrils and the deposition of fibrils and proteoglycans with the cell layer. Without wishing to be bound to a particular theory, one possible explanation is that the agarose provided a semi-permeable barrier that kept the secreted procollagen as well as the processing enzymes at or near the keratocytes surface leading to efficient processing to collagen and subsequent fibril and matrix assembly.

The processing of procollagen with subsequent fibril and matrix assembly in the cell layer associated with culture under an agarose overlay generated a corneal stroma-like architecture. Again, without wishing to be bound to a particular theory, we can speculate that the processing of procollagen and matrix deposition resulted in a substrate with which the keratocytes could interact. These keratocytes-matrix interactions favored the keratocytes phenotype and drove cornea-like organization. After the deposition of an extracellular matrix, the keratocytes became stratified as parallel oriented layers. It is probable that this keratocyte organization is due to the deposition of a stromal extracellular matrix that drives cell migration and organization. The intercellular spaces between the layers of keratocytes contain a well organized matrix. The collagen fibrils have small homogeneous diameters and are regularly packed. We suggest that this stroma-like architecture is generated by regulated assembly. This begins with normal pro collagen processing and fibril formation involving collagen types I and V, and includes the interaction of the assembling fibrils with decorin, lumican and keratocan. These interactions would regulate the later stages in fibril formation as well as packing.

Chondrocytes in cell culture without agarose encapsulation readily synthesize procollagen type II and deposit it into the culture media. Encapsulation of chondrocytes in agarose was originally used to enhance the differentiation of chondrocytes in culture and was later shown to also promote the formation of the chondrocyte pericellular matrix, which would contain collagen (Chang et al. 1997). Thus, agarose encapsulation might be enhancing procollagen type II processing to collagen by chondrocytes in culture as well.

Agarose overlay differs from agarose encapsulation. The encapsulation method is done on unattached cells or clumps of cells in suspension and results in the formation of tiny spheres containing cells and their associated matrix. The overlay method described here is done on cells that are attached to a substrate. The keratocytes in this report are attached to the bottom of a culture dish and the overlay results in the formation of a sheet of cells and their associated matrix. Furthermore, with the overlay method, the thickness and diameter of the resulting sheet could be varied by the initial plating density and size of the culture dish.

The processing of procollagen to collagen is thought to take place on the plasma membrane or cell surface [for review see (Canty and Kadler, Procollagen trafficking, processing and fibrillogenesis. J Cell Sci (2005) 118: 1341-1353)]. Dextran and other high molecular weight neutral polymers have been shown to increase the processing of procollagen and its deposition with the cell layer in cell culture [this report and (Bateman et al. 1986; Bateman et al. 1987)]. These agents are thought to act by a volume exclusion mechanism to increase the concentration of macromolecules in a solution (Atha and Ingham, Mechanism of precipitation of proteins by polyethylene glycols. Analysis in terms of excluded volume. J Biol Chem (1981) 256:12108-12117). Their presence would reduce the space that is available for large molecules, such as procollagen, but not for small molecules, such as salts and amino acids. Thus, for the processing of procollagen, the presence of these crowding agents in the media would increase the concentration of procollagen on the surface of the cells where the proteases are that clip off its globular domains.

Agarose has not been considered to be a crowding agent but it is routinely used as a molecular sieve to separate proteins and nucleic acids according to their size. A layer of agarose over cells in culture would therefore act as a semipermeable membrane to retard the diffusion of secreted macromolecules, such as procollagen, into the media and, as a result, the concentration of procollagen would increase on the surface of the cells where collagen processing takes place. The difference between an agarose overlay and dextran in solution is that the agarose, because it is insoluble, is a physical presence that would put some degree of confinement on the cell layer that could alter cell-cell interactions or cell movement.

Collagen binds to fibronectin and collagen fibril formation is facilitated by the presence of the integrin receptors for fibronectin, the presence of fibronectin and the formation of fibronectin fibrils [for review see (Canty and Kadler 2005)]. The agarose overlay also would act to increase the concentration of fibronectin on the cell surface and this could increase its assembly into fibrils as well as its binding to collagen and to its receptor. Type V collagen has been shown to nucleate collagen fibril formation and absence of type V collagen results in an embryonic lethal phenotype due to lack of fibril formation in the presence of normal type I collagen concentrations (Wenstrup et al., Type V collagen controls the initiation of collagen fibril assembly. J Biol Chem (2004) 279:53331-53337). It was suggested that this nucleation involves a regulatory interaction at or near the cell surface involving a molecular complex. Integrin frequency and distribution on the plasma membrane of the cell may play a role in determining the architectural arrangement of an extracellular matrix by positioning these regulatory complexes. This agarose overlay method will likely be a useful tool for studying cell-specific extracellular matrix assembly in vitro.

Example 2

Growth Factor-Specific Extracellular Matrix Formation by Keratocytes Cultures Under Agarose We have shown that IGF-I, TGF-β, and PDGF, but not FGF-2, stimulate collagen synthesis by keratocytes in culture. We have also shown that culturing insulin activated keratocytes under a thin layer of agarose increases the processing of procollagen to collagen and increases ECM formation. ECM formation by keratocytes cultured in these growth factors and under agarose is now evaluated.

Collagenase-isolated keratocytes from bovine corneas were plated at 40,000 cells/cm2 and then cultured with DMEM/F12 alone, or DMEM/F12 supplemented with either 10 ng IGF-I, 2 ng TGF-β, 10 ng FGF-2, or 10 ng PDGF/ml, all with ascorbate. Cultures were overlaid with ~1 mm of 3% agarose on day 4 and harvested for analysis on day 12. Keratocytes cell number was determined by measuring DNA content (cyquant assay). Collagen was determined by pepsin digestion, SDS/PAGE, simply blue staining, and by western blots with antibodies to procollagen I and III. ECM morphology was evaluated by electron microscopy.

Compared to cultures without an agarose overlay, cultures with an agarose overlay had a 50%-89% reduction in levels of procollagen in the media. Conversely, agarose cultures had higher levels of collagen type I deposited with the cell layer, IGF-I was 9.1 fold higher; TGF-β was 6.2 fold higher; PDGF was 2.8 fold higher; DMEM/F12 was 2.5 fold higher; and FGF-2 was 0.6 fold higher. Electron microscopy showed that the FGF-2 agarose cultures had little or no ECM and the keratocytes were in close cell contact while IGF-I agarose cultures had the least cell contact with an extensive fibrillar ECM. TGF-β agarose cultures had both a fibrillar and amorphous ECM. Accordingly, agarose overlay increases ECM formation with the cell layer only when the synthesis of collagen was stimulated and that the ECM morphology is growth factor specific.

Materials and Methods

Briefly:

Plate out cells in a tissue culture dish and add media containing a growth factor, such as IGF-I or insulin, that stimulate collagen synthesis. Prepare a 6% solution of low melting temperature agarose in distilled water. Dissolve and sterilize the agarose in an autoclave. Reduce the temperature of the agarose solution to 37 degrees in a water bath and mix with an equal volume of 2× tissue culture media containing 2× growth factor to make the agarose overlay solution. Remove the media from the dish containing the growth factor stimulated cells and add sufficient volume (1 ml for a 35 mm tissue culture dish) of the agarose overlay solution to form a layer ~1 mm thick on top of the cells. Allow the agarose to solidify at room temperature, add tissue culture media containing the growth factor to the dish and place the dish in a tissue culture incubator.

Materials and Methods—Detailed

Reagents.

All chemicals and growth factors were purchased from Sigma-Aldrich (St. Louis, Mo.) unless otherwise indicated. CyQuant kits, polyacrylamide gels, electrophoresis solutions, nitrocellulose, and DMEM/F12 were obtained from Invitrogen (Carlsbad, Calif.), Costar cell culture plates from Fisher Scientific (Suwanee, Ga.), Amicon 10,000 MWCO spin concentrators from Millipore Corporation (Bedford, Mass.), endo-β-galactosidase and chondroitinase ABC from Associates of Cape Cod (East Falmouth, Mass.) and ECL Western blotting analysis system from GE Healthcare (Piscataway, N.J.)

Isolation and Culture of Keratocytes.

Freshly harvested eyes from 1-2 year old cows were purchased from Pel Freeze (Rogers, Ark.) and shipped on wet ice by overnight delivery. The corneas were removed and the keratocytes isolated from the corneas by using two sequential collagenase digestions as previously described (Berryhill et al. 2001). The culture medium used throughout was DMEM/F12 supplemented with antibiotics and 1 mM 2-phospho-L-ascorbic acid (DMEM/F12). Media was adjusted to contain 100,000 cells/ml and 2 mls were plated/well on day zero in each of 4 wells of a 6 well plate (~20,000-cells/cm2), except where specified when 2 mls were plated in each well of a 24 well plate (~100,000-cells/cm2). Plates were incubated overnight at 37° C. in a humidified atmosphere containing 5% CO2 to allow the cells to attach. The medium was changed on day 1 to DMEM/F12 or to DMEM/F12 containing either 10 ng IGF-I, 10 ng IGF-II or 10 µg insulin/ml. The media was also supplemented with 5 g of dextran (MR~40,000, Fluka, 31389)/100 ml of media in one set of experiments. Media was removed and replaced with fresh media on days 4, 7, and 10 except where specified. Cultures were harvested for analysis on days 1, 4, 7, 10 and 13. Medium from 4 wells was removed and combined. The media and plates were stored at −80° C.

Media containing 3% agarose (low melting-type, Type VII, Sigma, A9045) also was prepared and over-layered on keratocytes that previously had been plated in a 24 well plate and cultured in media containing insulin for days 1 through 4. Agarose (6 g) was dissolved in 100 ml of distilled water by autoclaving, cooled to 37° C. in a water bath and mixed with an equal volume of 2×DMEM containing 20 µg of insulin/ml that had been warmed to 37° C. The resulting media containing 3% agarose was maintained at 37° C. Media was removed from the 24 well plate containing keratocytes and 0.2 ml of the 3% agarose was layered on top of the cells in each well. The agarose was allowed to solidify at room temperature, 2 mls of media containing insulin was added to the well and the plates returned to the incubator. Cultures were harvested, without intervening media changes, on days 7, 10, and 13 or on days 8 and 13.

DNA Measurements.

The DNA content of the cells in each well was determined using a CyQuant kit and following the vendor's instructions. Calf thymus DNA was used as a standard.

Pepsin Digestion of Media and Cell Layers.

Harvested media combined from 4 wells (8 ml) was cooled on ice and adjusted to 0.5 M acetic acid by the addition of 230 µl of glacial acetic acid followed by the addition of 100 µl of a pepsin stock solution (4 mg pepsin/ml 0.5 M acetic acid). Cold 0.5 M acetic acid (2 ml) containing 0.05 mg pepsin/ml was added to each well of 4 wells containing cells. Digestion of the media and cell layers was continued overnight at 4° C. The digests of the cell layers were combined and any insoluble material was removed by centrifugation. The digests were adjusted to neutrality with NaOH, dialyzed against deionized water, lyophilized and reconstituted in 100 µl of sample buffer (Invitrogen).

Extraction of Cell Layers.

Two mls of 0.5 M acetic acid or 250 µl of 4 M guanidine-HCl was added to each well containing cells and the cell layer extracted over night at 4° C. The wells were scraped; the extracts from 4 wells were combined and any insoluble material pelleted by centrifugation. The supernatant was dialyzed against deionized water. The acetic acid extracts and the guanidine extracts were used in Western blots to detect procollagen type I and proteoglycans, respectively.

Concentration of Media.

Media samples were used directly for detection of procollagen type I by Western blot. Media samples used for SDS/PAGE Simply Blue staining and for detection of core proteins were first concentrated to ⅒th volume using spin concentrators from Amicon. Aliquots of media and guanidine extracts of the cell layers were digested with endo-β-galactosidase or chondroitinase ABC according to the vendor's instructions for detection of lumican and keratocan core proteins or decorin core protein, respectively, by Western blot.

SDS/PAGE and Western Blot.

The size of the aliquots taken from the media, the cell layer extracts and the pepsin digests for electrophoresis on polyacrylamide gels was normalized to the DNA content of those cultures or to the DNA content of parallel cultures. This made it possible to directly compare the amount of a particular protein produced by the same number of cells. All samples were reduced prior to electrophoresis and were electrophoresed according to the vendor's instructions. Gels were stained for proteins using Simply Blue and Western blots were performed using the ECL Western blotting analysis system according to the vendor's instructions. Primary antibodies included: rabbit anti-sera to bovine lumican and to bovine keratocan (Berryhill et al., Production of prostaglandin D synthase as a keratan sulfate proteoglycan by cultured bovine keratocytes. Invest Ophthalmol Vis Sci (2001) 42:1201-1207), mouse monoclonal anti-decorin (DS1, Hybridoma Bank, U. of Iowa) and mouse monoclonal anti-procollagen type I (SP1.D8, Hybridoma Bank, U. of Iowa).

Electron Microscopy.

Cultured keratocytes were analyzed by transmission electron microscopy. Briefly, mono layers were fixed in 4% paraformaldehyde, 2.5% glutaraldehyde, 0.1 M sodium cacodylate pH 7.4, with 8.0 mM $CaCl_2$ (Birk and Trelstad 1984), post-fixed with 1% osmium tetroxide and dehydrated in a graded ethanol series. The agarose layer was removed before the 100% ethanol step. After dehydration in an ethanol series, the cells were infiltrated and embedded in a mixture of EMbed 812, nadic methyl anhydride, dodecenyl succinic anhydride and DMP-30 (Electron Microscopy Sciences, Hatfield, Pa.). Thin sections (90 nm) were cut using a Reichert UCT ultramicrotome and post-stained with 1% aqueous uranyl acetate and 1% phosphotungstic acid, pH 3.2. The sections were analyzed using a lEOL 1400 transmission electron microscope at 80 kV and digital images were captured with a Gatan Orius camera.

Statistics.

Statistical analysis was performed with four determined values for each point using Statview (SAS Institute, Cary, N.C.). Data are expressed as the mean±standard error. Significant differences were determined by paired t-test.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of enhancing the formation of extracellular matrices in culture comprising the steps of:
    plating out fibroblast cells on a tissue culture substrate;
    adding media containing a collagen synthesis stimulating growth factor to the plated cells;
    incubating the plated cells to facilitate attachment of the cells to the tissue culture substrate;
    removing the media from the substrate containing the growth factor stimulated cells;
    adding a volume exclusion agent capable of converting procollagen to collagen on top of the plated fibroblast cells wherein the volume exclusion agent is a hydrogel wherein the hydrogel creates a semipermeable barrier on the top of the plated fibroblast cells;
    adding tissue culture media containing the collagen synthesis stimulating growth factor on top of the hydrogel; and
    incubating the plated fibroblast cells in a tissue culture incubator;
    whereby after incubation procollagen is converted to collagen and extracellular matrices are formed.

2. The method according to claim 1, wherein the volume exclusion agent is an agarose overlay.

3. The method according to claim 2, wherein the agarose overlay is between a 1%-6% solution of low melting temperature agarose in distilled water mixed with an equal volume of media containing the collagen synthesis stimulating growth factor.

4. The method according to claim 1 wherein the fibroblast cells are selected from the group consisting of keratocytes, and tenocytes.

5. A method of enhancing the formation of extracellular collagen matrices in culture by increasing the conversion of procollagen to collagen comprising the steps of:
    plating out keratocytes on a tissue culture substrate;
    adding a volume exclusion agent capable of converting procollagen to collagen on top of the plated keratocytes wherein the volume exclusion agent is a hydrogel wherein the hydrogel creates a semipermeable barrier on the top of the plated keratocytes;
    adding tissue culture media containing a collagen synthesis stimulating growth factor to the substrate containing the overlaid plated keratocytes; and
    incubating the plated keratocytes in a tissue culture incubator
    whereby after incubation procollagen is converted to collagen and extracellular collagen matrices are formed.

6. The method according to claim 5, wherein the volume exclusion agent is an agarose overlay.

7. The method according to claim 6, wherein the agarose overlay is between a 1%-6% solution of low melting temperature agarose in distilled water.

8. A method of enhancing the formation of extracellular matrices in culture by increasing the conversion of procollagen to collagen comprising the steps of:
    plating out keratocytes on a tissue culture substrate;
    adding media containing a collagen synthesis stimulating growth factor to the plated keratocytes;
    incubating the plated keratocytes to facilitate attachment of the keratocytes to the tissue culture substrate;
    removing the media from the substrate containing the growth factor stimulated keratocytes;
    adding a hydrogel overlay capable of converting procollagen to collagen on top of the plated keratocytes wherein the hydrogel creates a semipermeable barrier on the top of the plated keratocytes;
    adding tissue culture media containing the growth factor to the substrate containing the overlaid plated keratocytes; and
    incubating the plated keratocytes in a tissue culture incubator;
    whereby after incubation procollagen is converted to collagen and extracellular collagen matrices are formed.

9. The method according to claim 8, wherein the growth factor is insulin.

10. The method of claim 1, wherein the growth factor is selected from the group consisting of IGF-I, PDGF, TGF-β and insulin.

11. The method of claim 1, wherein the volume exclusion agent is a hydrogel selected from the group consisting of agarose, kappa-carrageenan, iota-carrageenan, gelatin, elastin-mimetic protein polymers and silk-elastin block copolymers.

12. The method of claim 5, wherein the growth factor is selected from the group consisting of IGF-I, PDGF, TGF-β and insulin.

13. The method of claim 5, wherein the volume exclusion agent is a hydrogel selected from the group consisting of agarose, kappa-carrageenan, iota-carrageenan, gelatin, elastin-mimetic protein polymers and silk-elastin block copolymers.

14. The method of claim 8, wherein the growth factor is selected from the group consisting of IGF-I, PDGF, TGF-β and insulin.

15. The method of claim 8, wherein the volume exclusion agent is a hydrogel selected from the group consisting of agarose, kappa-carrageenan, iota-carrageenan, gelatin, elastin-mimetic protein polymers and silk-elastin block copolymers.

* * * * *